United States Patent [19]

Cipolli et al.

[11] Patent Number: 5,344,931
[45] Date of Patent: Sep. 6, 1994

[54] SALTS OF TRIAZINIC COMPOUNDS WITH PHOSPHORUS OXYACIDS, AND USE OF SAID COMPOUNDS IN SELF-EXTINGUISHING POLYMERIC COMPOSITIONS

[75] Inventors: Roberto Cipolli, Novara; Enrico Masarati, Castelnuovo Valtidone; Roberto Oriani, Milan; Mario Pirozzi, San Donato Milanese; Gilberto Nucida, San Giuliano Milanese, all of Italy

[73] Assignee: Ministero Dell'Universita' E Della Ricerca Scientifica E Technologica, Rome, Italy

[21] Appl. No.: 956,994

[22] Filed: Oct. 6, 1992

[30] Foreign Application Priority Data

Oct. 11, 1991 [IT] Italy .................. MI91A002705

[51] Int. Cl.$^5$ ........................... C07D 251/02
[52] U.S. Cl. ........................ 544/195; 524/100
[58] Field of Search ............. 544/195; 524/100, 416

[56] References Cited

U.S. PATENT DOCUMENTS

| | | | |
|---|---|---|---|
| 3,296,265 | 1/1967 | Garner | 544/195 |
| 4,154,930 | 5/1979 | Halpern | 544/195 |
| 4,201,705 | 5/1980 | Halpern | 544/195 |
| 4,393,207 | 7/1983 | Hummerich et al. | 544/196 |
| 4,408,045 | 10/1983 | Dobramysl et al. | 544/196 |
| 4,879,327 | 11/1989 | Poisson et al. | 544/195 |
| 5,159,074 | 10/1992 | Arndt et al. | 544/195 |
| 5,182,388 | 1/1993 | Cipolli et al. | 544/195 |

FOREIGN PATENT DOCUMENTS

| | | |
|---|---|---|
| 0014463 | 8/1980 | European Pat. Off. |
| 0286478 | 10/1988 | European Pat. Off. |
| 0415371 | 3/1991 | European Pat. Off. |
| 0448774 | 10/1991 | European Pat. Off. |
| 0453871 | 10/1991 | European Pat. Off. |
| 0466137 | 1/1992 | European Pat. Off. |
| 1286661 | 8/1972 | United Kingdom |

Primary Examiner—Kriellion S. Morgan
Attorney, Agent, or Firm—Oblon, Spivak, McClelland, Maier & Neustadt

[57] ABSTRACT

Salts of triazinic compounds with phosphorus oxyacids, having the general formula (I):

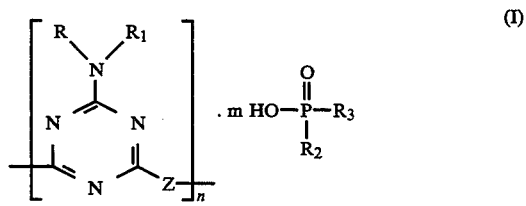

obtained by salifying oligomeric derivatives of 2,4,6-triamino-1,3,5-triazine with a phosphorus-containing acid.

The compounds with general formula (I) find use in particular as flame-retardant additives.

2 Claims, No Drawings

SALTS OF TRIAZINIC COMPOUNDS WITH PHOSPHORUS OXYACIDS, AND USE OF SAID COMPOUNDS IN SELF-EXTINGUISHING POLYMERIC COMPOSITIONS

The present invention relates to salts of triazinic compounds with phosphorus oxyacids.

More particularly, the present invention relates to salts of triazinic compounds with phosphorus oxyacids, and to their use in the preparation of self-extinguishing polymeric compositions based on thermo-plastic polymers, or on polymers with elastomeric properties, in particular olefinic polymers or copolymers.

In the art several solutions are known in order to reduce or eliminate the combustibility of polymers. Some of such solutions are based on the use of metal compounds, in particular of antimony, bismuth or arsenic, in combination with partially halogenated and thermally unstable organic compounds, such as chlorinated paraffinic waxes.

Other solutions are based on the use of substances able to produce intumescence. The formulations of intumescent type are generally constituted by the polymer and at least three main additives: an essentially phosphorus-containing additive, the purpose of which is of forming, during combustion, a semisolid, impermeable glassy layer essentially constituted by polyphosphoric acid, and of activating the process leading to intumescence formation; a second additive which contains nitrogen and performs the function of foaming agent; and a third additive, which contains carbon and acts as a carbon donor in order to form an insulating cellular carbonaceous layer (char) between the polymer and the flame.

Examples of such a type of intumescent formulations are those reported in the following patents: U.S. Pat. No. 3,810,862 (Phillips Petroleum Co.), based on melamine, pentaerythritol and ammonium polyphosphate; U.S. Pat. No. 4,727,102 (Vamp S.r.L.), based on melamine cyanurate, a hydroxyalkyl derivative of isocyanuric acid and ammonium polyphosphate; and published patent application WO 85/05626 (Plascoat U.K. Limited), based on several phosphorus and nitrogen, compounds among which, in particular, a combination of melamine phosphate, pentaerythritol and ammonium polyphosphate may be mentioned.

In more recent formulations, together with the use of an organic or inorganic phosphorus compound, a nitrogen-containing compound was used, which generally is an aminoplastic resin obtained by condensing urea, melamine or dicyandiamide with formaldehyde.

Examples of double-additive formulations are those reported in U.S. Pat. No. 4,504,610 (Montedison S.p.A.), based on oligomeric derivatives of 1,3,5-triazine and ammonium polyphosphate; and EP patent 14,463 (Montedison S.p.A.), based on organic compounds selected from among benzylguanamine and reaction products of aldehydes with various nitrogen-containing cyclic compounds, in particular benzylguanamine/formaldehyde copolymers, and ammonium polyphosphate.

Self-extinguishing compositions can also be obtained by using single-component additives, containing both nitrogen and phosphorus in one single organic molecule, as disclosed in U.S. Pat. No. 4,201,705 (Borg-Wagner Corp.).

These intumescent flame-retardant systems endow the polymer which contains them, with the property of originating a carbonaceous residue after a fire or a flame application. This kind or retardant systems display a number of advantages: absence of phenomena of corrosion in the machines on which the polymers are processed, lower smoke generation as compared to systems containing metal compounds and halogenated hydrocarbons, and, above all, the possibility of endowing the polymers with satisfactory flame-retardant properties with a smaller amount of total additive, and, consequently, without an excessive decay of the mechanical properties of the same polymers.

The present Applicant has found now that extremely good flame-retardant properties can be supplied to the above said polymers by means of the use of a category of simple-structure phosphorus-nitrogen-containing compounds, based on oligomeric derivatives of 2,4,6-triamino-1,3,5-triazine salified with a phosphorus-containing acid.

The novel additives make it also possible, when suitably mixed with ammonium and/or amine phosphates and/or phosphonates, polymeric compositions to be obtained which are endowed with excellent self-extinguishing characteristics with a lower total content of additives as compared to the prior art, and, therefore, with a further contribution to the preservation of chemical and physical properties of the polymers in question.

The present Applicant has furthermore evidenced that the reaction of salification of oligomeric derivatives of 2,4,6-triamino-1,3,5-triazine with phosphorus oxyacids not only makes it possible—as it was obvious—the amount of ammonium or amine phosphate and/or phosphonate to be reduced, but also self-extinguishment levels to be reached which could not be obtained by simply using the oligomeric triazinic derivatives with ammonium or amine phosphates and/or phosphonates.

The novel additives furthermore display good stability to heat, hence retaining a high activity as flame-retardants also after the high-temperature fabrication processes the polymeric compositions which contain them are submitted to.

The polymeric compositions containing the phosphorus-nitrogen additives according to the present invention furthermore show the advantage of giving rise, in the case of a fire, to a very moderate and non-obscuring smoke emission.

Therefore, the object of the instant invention are the salts with general formula (I):

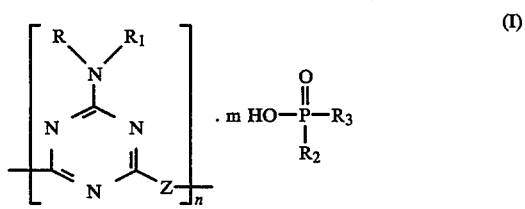

wherein:
R is H or

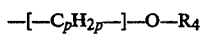

in which
p is an integer comprised within the range of from 2 to 8, and preferably of from 2 to 4; and $R_4$ is H; $(C_1-C_8)$-alkyl; preferably H or $(C_1-C_4)$-alkyl; $(C_2-C_8)$-alkenyl; $-[-C_qH_{2q}-]-O-R_5$ in which q is an integer comprised within the range of from 1 to 4; and $R_5$ is H or $(C_1-C_4)$-alkyl; $(C_6-C_{12})$-cycloalkyl or alkylcycloalkyl;

$R_1$ is $(C_1-C_4)$-alkyl or R;

or the moiety:

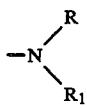

is replaced by a heterocyclic radical bonded to the triazinic ring through the nitrogen atom;

n is an integer comprised within the range of from 2 to 50;

m is a numeral smaller than, or equal to, n; in particular, the ratio of m/n is comprised within the range of from 0.5 to 1;

Z is a divalent or polyvalent radical falling within the scope of one of following formulae:

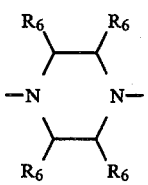 (II)

wherein the $-R_6$ radicals, which may be the same, or different from each other, are hydrogen or $(C_1-C_4)$-alkyl;

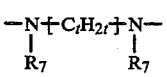 (III)

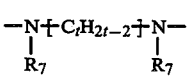 (IV)

wherein t is an integer comprised within the range of from 2 to 14; $R_7$ is hydrogen, $(C_1-C_4)$-alkyl, $(C_2-C_6)$-alkenyl, $(C_1-C_4)$-hydroxyalkyl;

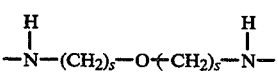 (V)

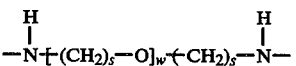 (VI)

wherein s is an integer comprised within the range of from 2 to 5 and w is an integer comprised within the range of from 1 to 3;

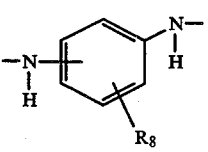 (VII)

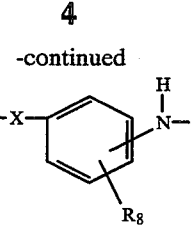 (VIII)

wherein:

X is a direct $-C-C-$; O; S; S$-$S; SO; $SO_2$; NH, $NHSO_2$; NHCO; N=N; $CH_2$ bond;

$R_8$ is hydrogen; hydroxy; $(C_1-C_4)$-alkyl; $(C_1-C_4)$-alkoxy;

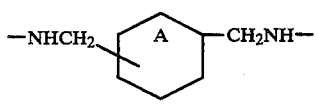 (IX)

wherein "A" can be a saturated or unsaturated cycle;

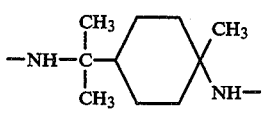 (X)

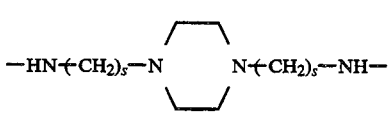 (XI)

wherein s has the above defined meaning;

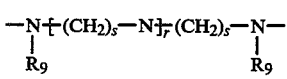 (XII)

wherein:

$R_9$ is hydrogen or $(C_1-C_4)$-alkyl;

r is an integer comprised within the range of from 1 to 5;

the indexes s, which are the same, or may be different from each other, have the above defined meaning;

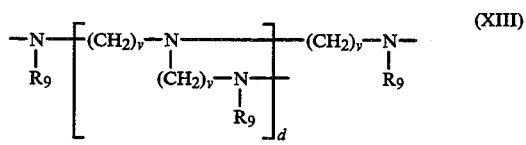 (XIII)

wherein:

$R_9$ has the above defined meaning;

v is an integer comprised within the range of from 2 to 4;

d is either 1 or 2;

$R_2$ is H; OH; $-O-(C_1-C_8)$-alkyl; $-O-(C_6-C_{12})$-aryl, possibly substituted with a $(C_1-C_8)$-alkyl; $(C_7-C_{16})$-aralkyl; $(C_1-C_4)$-alkyl possibly substituted with a carboxy group; $(C_6-C_{12})$-aryl;

$R_3$ is H; OH; $-O-(C_1-C_8)$-alkyl; $-O-(C_6-C_{12})$-aryl, $(C_1-C_4)$-alkyl; $(C_6-C_{12})$-aryl;

$R_3$ furthermore is:

$$\begin{array}{c} R_{10} \ \ O \\ | \ \ \ \ \ \| \\ -C-P-OH \\ | \ \ \ \ \ | \\ Y \ \ \ \ OH \end{array}$$

wherein:
$R_{10}$ is hydrogen or $(C_1-C_{12})$-alkyl;
Y is OH or $R_{10}$;

$$\begin{array}{c} R_{10} \ \ O \\ | \ \ \ \ \ \| \\ -C-P-OH \\ | \ \ \ \ \ | \\ N \ \ \ OH \\ / \ \backslash \\ R_{11} \ \ R_{11} \end{array}$$

wherein:
$R_{10}$ has the same meaning as defined hereinabove and $R_{11}$ radicals, which are the same, or may be different from each other, are hydrogen or $(C_1-C_4)$-alkyl;
or the moiety:

$$-N\begin{array}{c} R_{11} \\ \backslash \\ / \\ R_{11} \end{array}$$

is replaced by a heterocyclic radical bonded to the carbon atom through the nitrogen atom and possibly containing another heteroatom preferably selected from O, S, N;

$$\left[ \begin{array}{c} O \\ \| \\ -O-P-OH \\ | \\ OR_{12} \end{array} \right]_w$$

wherein:
$R_{12}$ is hydrogen or $(C_1-C_8)$-alkyl; and
w has the same meaning as defined hereinabove;

$$\left[ \begin{array}{c} O \\ \| \\ -CH-CH-P-OH \\ | \ \ \ \ \ \ \ \ \ | \\ R_{13} \ \ \ \ \ \ \ OH \end{array} \right]_2$$

wherein:
$R_{13}$ is hydrogen or hydroxy;

$$\begin{array}{c} O \\ \| \\ -CH_2-CH-CH_2-P-OH; \\ | \ \ \ \ \ \ \ \ \ \ \ \ \ \ \ | \\ O=P-OH \ \ \ \ OH \\ | \\ OH \end{array}$$

$$-CH_2-N\left[ \begin{array}{c} O \\ \| \\ CH_2-P-OH \\ | \\ OH \end{array} \right]_2;$$

$$-CH_2-N(CH_2)_uN\left[ \begin{array}{c} O \\ \| \\ CH_2-P-OH \\ | \\ H \end{array} \right]_2;$$

with $CH_2$, $O=P-OH$, $OH$ branch $$-CH_2-N(CH_2)_u-N(CH_2)_u-N\left[ \begin{array}{c} O \\ \| \\ CH_2-P-OH \\ | \\ OH \end{array} \right]_2;$$

with $CH_2$ branches and $O=P-OH$, $OH$ groups wherein:
u has the same meaning as defined above;
or
$R_2$ and $R_3$, taken together, may constitute a cyclic structure having the formula:

$$\begin{array}{c} -O-CH_2 \ \ \ \ \ CH_3 \\ \ \ \ \ \ \ \ \ \ \ \ \ \backslash \ / \\ \ \ \ \ \ \ \ \ \ \ \ \ \ C \\ \ \ \ \ \ \ \ \ \ \ \ \ / \ \backslash \\ -O-CH_2 \ \ \ \ \ CH_3 \end{array};$$

$$\begin{array}{c} -O-CH_2 \ \ \ \ CH_2O \ \ O \\ \ \ \ \ \ \ \ \ \ \ \ \backslash \ \ \ \ \ / \ \ \ \ \backslash \ \| \\ \ \ \ \ \ \ \ \ \ \ \ \ C \ \ \ \ \ \ \ \ \ \ P-OH. \\ \ \ \ \ \ \ \ \ \ \ \ / \ \ \ \ \backslash \ \ \ \ / \\ -O-CH_2 \ \ \ \ CH_2O \end{array}$$

Examples or R radical, in general formula (I), are:
2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethyl-hexyl; 7-hydroxyheptyl; 7-hydroxyoctyl; 2-methoxyethyl; 2-methoxypropyl; 3-methoxypropyl; 4-methoxybutyl; 6-methoxyhexyl; 7-methoxyheptyl; 7-methoxyoctyl; 2-ethoxyethyl; 3-ethoxypropyl; 4-ethoxy-butyl; 3-propoxypropyl; 3-butoxypropyl; 4-butoxybutyl; 4-isobutoxybutyl; 5-propoxypentyl; 2-cyclohexyloxy-ethyl; 2-ethenyloxyethyl; 2-(2-hydroxyethoxy)-ethyl; 2-(2-methoxyethoxy)-ethyl; and so forth.

Examples of $R_1$ radical are, besides those as defined for R: methyl; ethyl; propyl; isopropyl; butyl; isobutyl; tert.-butyl.

Examples of heterocyclic radicals which may replace the moiety:

$$-N\begin{array}{c} R \\ \backslash \\ / \\ R_1 \end{array}$$

are:
aziridine; pyrrolidine; piperidine; piperazine.

Examples of —Z— radicals are those deriving, by means of the removal of a hydrogen atom from each reacted amino group, from the following compounds: piperazine; 2-methyl-piperazine; 2,5-dimethyl-piperazine; 2,3,5,6-tetramethyl-piperazine; 2-ethyl-piperazine; 2,5-diethylpiperazine; 1,2-diaminoethane; 1,3-diaminopropane; 1,4-diaminobutane; 1,5-diamino-pentane; 1,6- diaminohexane; 1,8-diamino-octane; 1,10-diaminodecane; 1,12-diaminododecane; N,N'-dimethyl-1,2-diaminoethane; N-methyl-1,3-diaminopropane; N-ethyl-1,2-diaminoethane; N-isopropyl-1,2-diaminoethane; N-(2-hydroxyethyl)-1,2-diaminoethane; N,N'-bis-(2-hydroxyethyl)-1,2-diaminoethane; N-(2-hydroxyethyl)-1,3-diaminopropane; n-hexenyl-1,6-diaminohexane; N,N'-diethyl-1,4-diamino-2-butene; 2,5-diamino-3-hexene; 2-aminoethylether; (2-aminoethoxy)-methylether; 1,2-bis-(2-aminoethoxy)-ethane; 1,3-diaminobenzene; 1,4-di-aminobenzene; 2,4-diaminotoluene; 2,4-diaminoanisole; 2,4-diaminophenol; 4-aminophenylether; 4,4'-methylene-dianiline; 4,4'-diaminobenzanilide; 3-aminophenylsulfone; 4-aminophenylsulfone; 4-aminophenylsulfoxide; 4-aminophenyldisulfide; 1,3-bis-(aminomethyl)benzene; 1,4-bis(aminomethyl)benzene; 1,3-bis(aminomethyl)-cyclohexane; 1,8-diamino-p-menthane; 1,4-bis(2-aminoethyl)-piperazine; 1,4-bis(3-aminopropyl)piperazine; 1,4-bis(4-aminobutyl)piperazine; 1,4-bis-(5-aminopentyl)piperazine; bis-(2-aminoethyl)-amine; bis(3-aminopropyl)amine; bis(4-aminobutyl)amine; bis-(5-aminopentyl)amine; bis[2-(N-methylamino)-ethyl]-amine; 2-N-butyl-bis-(2-aminoethyl)-amine; bis[3-(N-methylamino)-propyl]-amine; N-(3-aminopropyl)-1,4-di-aminobutane; N-(3-aminopropyl)-1,5-diaminopentane; N-(4-aminobutyl)-1,5-diaminopentane; tris(2-aminoethyl)-amine; tris(3-aminopropyl)-amine; tris(4-aminobutyl)-amine; tris[2-(N-ethylamino)-ethyl]-amine; N,N'-bis(2-aminoethyl)-1,2-diaminoethane; N,N'-bis(3-aminopropyl)-1,3-diaminopropane; N,N'-bis(2-aminoethyl)-1,3-diamino-propane; N,N'-bis(3-aminopropyl)-1,2-diaminoethane; N,N'-bis(3-aminopropyl)-1,4-diaminobutane; bis-[2-(2-aminoethyl)-aminoethyl]-amine; N,N'-bis[2-(2-aminoethyl)-aminoethyl]-1,2-diaminoethane; N,N'-bis[3-(2-aminoethyl)-aminopropyl]-1,2-diaminoethane; N,N,N',N'-tetrakis-(2-aminoethyl)-1,2-diaminoethane; and so forth.

Examples of phosphorus containing acids are: hypophosphorous acid; phosphorous acid; phosphoric acid; pyrophosphoric acid; tripolyphosphoric acid; ethane-1,1,2-triphosphonic acid; 2-hydroxyethane-1,1,2-triphosphonic acid; propane-1,2,3-triphosphonic acid; isopropylphosphoric acid; n-butylphosphoric acid; di-n-butylphosphoric acid; di-isopropylphosphoric acid; di-n-pentylphosphoric acid; isooctylphosphoric acid; hexylphosphoric acid; 2-ethylhexylphosphoric acid; methylphosphonic acid; ethylphosphonic acid; n-propylphosphonic acid; n-butylphosphonic acid; aminomethylphosphonic acid; phenylphosphoric acid; phenylphosphonic acid; phenylphosphinic acid; di-n-butylpyrophosphoric acid; di-(2-ethylhexyl)pyro-phosphoric acid; octylphenylphosphoric acid; 2-methylbenzylphosphonic acid; 1-aminoethane-1,1-diphosphonic acid; 1-hydroxyethane-1,1-diphosphonic acid; 1-hydroxydodecane-1,1-diphosphonic acid; 1-(N-methylamino)-ethane-1,1-diphosphonic acid; N,N-dimethylaminoethane-1,1-diphosphonic acid; N-butyl-aminomethane-1,1-diphosphonic acid; phosphonoacetic acid; 2-phosphonopropionic acid; 3-phosphonopropionic acid; 2-phosphonobutyric acid; 4-phosphonobutyric acid; 2-hydroxy-5,5-dimethyl-2-oxo-1,3,2-dioxophosphorinane; 3,9-dihydroxy-2,4,8,10-tetraoxo-3,9-diphosphaspiro-[5,5]-undecane-3,9-dioxide; amino-tris(methylenephosphonic) acid; ethylenediaminotetra(methylenephosphonic) acid; hexamethylenediaminotetra(methylenephosphonic) acid; diethylenetriaminopenta(methylenephosphonic) acid; and so forth.

Specific compounds falling within the scope of formula (I) are reported in the Examples which follow the instant disclosure.

The products of general formula (I) can be synthetized by reacting—in the presence of a suitable solvent (such as, e.g., water, methyl alcohol, ethyl alcohol, acetonitrile,) at temperatures comprised within the range of from 0° C. to the boiling point of the solvent used—an oligomeric derivative of 2,4,6-triamino-1,3,5-triazine, having the general formula (XIV):

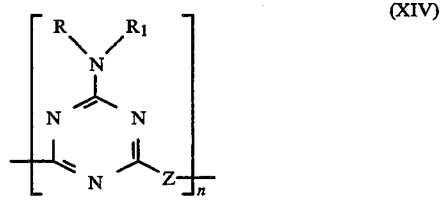

wherein R, $R_1$, Z and n have the same meaning as defined hereinabove, with a phosphorus-containing acid having the general formula (XV):

wherein $R_2$ and $R_3$ have the same meaning as defined hereinabove, or, if the phosphorus-containing acid may act as a solvent, in the absence of solvents and with an excess of phosphorus-containing acid, at temperatures comprised within the range of from 0° to 150° C.

The resulting salt product can be easily separated from the reaction mass by filtration, or by distilling off the solvent.

In general, products of general formula (I) are obtained as crystalline powders of white colour, which are of good quality and can be used in self-extinguishing composition without any further purification steps.

Some of the intermediates of general formula (XIV) are known; however, they can be easily synthetized according to the general method schematically shown hereinunder:

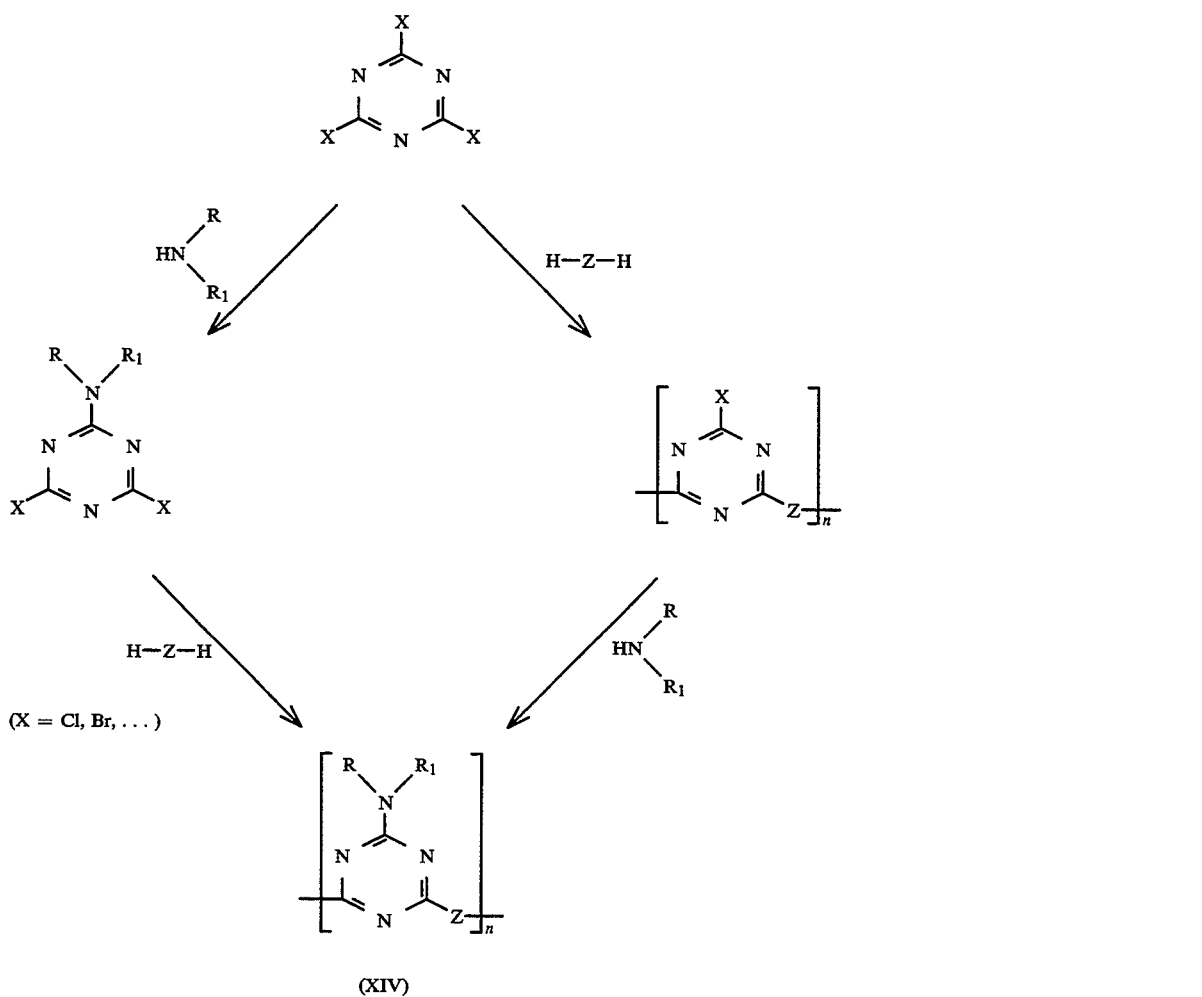

or according to as disclosed in Italian patent application No. 21 456 A/90 filed by the present Applicant on Sep. 13th, 1990.

Also the phosphorus-containing acids having the general formula (XV) are known, and many of them are also available in commercial amounts.

Another object of the present invention are the self-extinguishing polymeric compositions comprising:

(a) from 90 to 40 parts by weight of a thermoplastic polymer, or of a polymer endowed with elastomeric properties;

(b) from 7 to 28, preferably from 8 to 25, parts by weight of one or more ammonium or amine phosphate(s) or phosphonate(s);

(c) from 3 to 32, preferably from 4 to 25, parts by weight of one or more oligomeric derivative(s) of 2,4,6-triamino-1,3,5-triazine salified with a phosphorus oxyacid, said oligomeric derivatives of 2,4,6-triamino-1,3,5-triazine having the general formula (XIV):

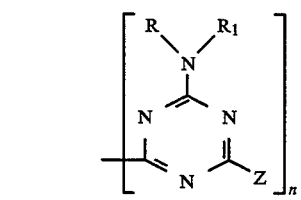

wherein R, $R_1$, Z and n have the same meaning as defined hereinabove.

The (c) component is preferably selected from the salts having the general formula (I):

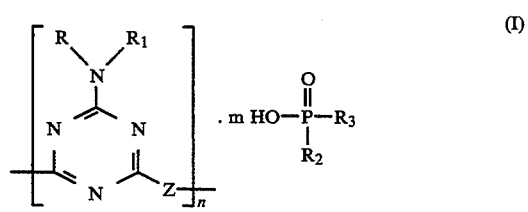

wherein the radicals from R to $R_3$, Z, n and m have the same meaning as defined hereinabove.

Particularly preferred are the salts of those compounds of general formula (XIV), wherein the R radical is replaced by a

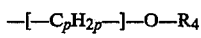

moiety, in which p is an integer comprised within the range of from 2 to 4 and $R_4$ is hydrogen or $(C_1-C_4)$-alkyl; or $R_1$ radical is hydrogen, or the moiety:

is replaced by an $—NH_2$ radical or a heterocyclic radical selected from among aziridine, pyrrolidine, piperidine, piperazine.

Among the phosphates, those ammonium polyphosphates are preferred which fall within the scope of the general formula

in which n represents and integer equal to, or larger than, 2; preferably, the molecular weight of polyphosphates should be high enough, in order to secure a low solubility in water. For indicative purposes, n is preferably comprised within the range of from 2 to 500.

The composition of the polyphosphates having the formula indicated hereinabove, in which n is a large enough numeral and is preferably comprised within the range of from 50 to 500, practically is the composition which corresponds to the formula of metaphosphates $(NH_4PO_3)_n$.

An example for such polyphosphates is the product known under the trade name "Exolit 422" (manufactured and marketed by Hoechst) and having the composition $(NH_4PO_3)_n$, in which n is larger than 50; another example is the product known under the trade name "Phos-Chek P/30" (Monsanto Chemical) and having an analogous composition.

Another polyphosphate which may be advantageously used, above all thanks to its low solubility in water, is the product known under the trade name "Exolit 462" (manufactured and marketed by Hoechst) and corresponding to Exolit 422 microencapsulated in melamine-formaldehyde resin.

Other phosphates which can be used are those deriving from amines, such as, e.g., dimethylammonium or diethylammonium phosphate, ethylenediamine phosphate, melamine ortho- or pyrophosphate.

Among phosphonates, extremely good results were obtained by using those (mono- or poly-substituted) ammonium phosphonates which are derived from mono- and poly-phosphonic acids, examples of which are: ethane-1,1,2-triphosphonic acid; 2-hydroxyethane-1,1,2-triphosphonic acid; propane-1,2,3-triphosphonic acid; methyl-phosphonic acid; ethyl-phosphonic acid; n-propylphosphonic acid; n-butylphosphonic acid; phenylphosphonic acid; 1-amino-ethane-1,1-diphosphonic acid; 1-hydroxyethane-1,1-diphosphonic acid; 1-hydroxydodecane-1,1-diphosphonic acid; phosphonoacetic acid; 2-phospho-nopropionic acid; 3-phosphono-propionic acid; 2-phospho-nobutyric acid; 4-phosphonobutyric acid; amino-tris(methylenephosphonic) acid; ethylenediaminotetra(methylenephosphonic) acid; hexamethylenediaminotetra(methylenephosphonic) acid; diethylenetriaminopenta(methylenephosphonic) acid; and so forth.

Among the polymers which can be used in the compositions according to the present invention, those polymers and copolymers of olefines are preferred which have the general formula

in which R is a hydrogen atom, or a $C_1-C_8$ alkyl or aryl radical; in particular:

1. isotactic or prevailingly isotactic polypropylene;
2. HDPE, LLDPE, LDPE polyethylene;
3. crystalline propylene copolymers containing minor proportions of ethylene and/or other alpha-olefins, such as, e.g., 1-butene, 1-hexene, 1-octene, 4-methyl-1-pentene;
4. heterophasic compositions comprising
   (A) a fraction consisting of a propylene copolymer, or of one of the copolymers according to (3); and
   (B) a copolymeric fraction formed by elastomeric copolymers of ethylene with an alpha-olefin, possibly containing minor proportions of a diene, with said alpha-olefin being preferably selected from propylene and 1-butene;
5. elastomeric copolymers of ethylene with alpha-olefins possibly containing minor proportions of a diene.

Examples of dienes which are more commonly used in said elastomeric copolymers are butadiene, ethylidene-norbornene, hexadiene-1,4.

Among the polymers of olefins with formula

in which R is an aryl radical, "Crystal" and impact resistant polystyrene are preferred.

Other examples of polymers which can be commonly used are acrylonitrile/butadiene/styrene (ABS) and styrene/acrylonitrile (SAN) copolymers; (polyester and polyether) polyurethane; poly-(ethylene terephthalate); poly-(butylene terephthalate) and polyamides.

The self-extinguishing compositions according to the present invention can be prepared by means of methods known from the prior art: for example, ammonium or amine phosphate or phosphonate is first intimately mixed with one or more salts of the compounds of general formula (XIV) in finely subdivided form (with their particles being preferably smaller than 70 micrometers) and the resulting mixture is added to the polymer in a turbomixer, in order to produce a homogeneous blend which is subsequently extruded and pelletized. The granular product obtained in that way can be transformed into various articles of manufacture by means of any of the well-known, available moulding techniques.

The flame-retardant additives according to the present invention are also suitable for use in the field of flame-retardant paints.

Oligomeric compounds with salt character falling within the scope of general formula (I) not cited in the examples, but equally advantageously useable in the self-extinguishing polymeric compositions according to the present invention, are those reported in following Table 1.

TABLE 1

| Compounds | R—N—R$_1$ | | —Z— | n | m/n | $\text{HO-}\underset{\underset{R_2}{\mid}}{\overset{\overset{O}{\parallel}}{P}}\text{-R}_3$ |
|---|---|---|---|---|---|---|
| 1 | CH$_2$CH$_2$OH | CH$_2$CH$_2$OH | —N(piperazine)N— | 14 | 0.7 | H$_3$PO$_3$ |
| 2 | CH$_2$CH$_2$OH | CH$_3$ | —N(piperazine)N— | 15 | 1 | H$_3$PO$_4$ |
| 3 | CH$_2$CH$_2$OC$_2$H$_5$ | H | —NHCH$_2$—(cyclohexyl)—CH$_2$NH— | 13 | 1 | H$_3$PO$_4$ |
| 4 | (CH$_2$)$_5$OH | H | —N(piperazine)N— | 18 | 0.6 | HO-P(=O)(H)-C$_6$H$_5$ |
| 5 | CH$_2$CH$_2$OCH$_3$ | H | N(CH$_2$CH$_2$—NH—)$_3$ | 12 | 1 | H$_3$PO$_4$ |
| 6 | CH$_2$CH—OH<br>           CH$_3$ | H | —N(piperazine)N— | 21 | 0.4 | (HO)$_2$P(=O)—C(C$_{11}$H$_{23}$)(OH)—P(=O)(OH)$_2$ |
| 7 | CH$_2$CH$_2$OCH=CH$_2$ | H | —N(piperazine)N— | 20 | 1 | H$_3$PO$_4$ |
| 8 | H | H | —N(piperazine)N— | 15 | 0.7 | HO-P(=O)(OCH$_2$-C(CH$_3$)$_2$-CH$_2$O) (cyclic) |
| 9 | (CH$_2$)$_2$O(CH$_2$)$_2$OCH$_3$ | H | —N(piperazine)N— | 14 | 1 | H$_3$PO$_4$ |
| 10 | H | H | —HNCH$_2$CH$_2$NH— | 17 | 0.5 | HO-P(=O)(OH)(O-nC$_4$H$_9$) 40%<br>HO-P(=O)(O-nC$_4$H$_9$)(O-nC$_4$H$_9$) 60% |
| 11 | CH$_2$CH$_2$OCH$_3$ | H | —N(CH$_3$)—CH$_2$CH$_2$—N(CH$_3$)— | 18 | 1 | H$_3$PO$_3$ |
| 12 | CH$_2$CH$_2$O-(cyclohexyl) | H | —N(piperazine)N— | 15 | 0.8 | H$_3$PO$_4$ |
| 13 | CH$_2$CH$_2$OCH$_3$ | H | —HN(CH$_2$)$_2$N(CH$_2$)$_2$N(CH$_2$)$_2$NH— | 11 | 0.5 | H$_3$PO$_4$ |
| 14 | H | H | —N(CH$_2$CH$_2$OH)—CH$_2$CH$_2$—N(CH$_2$CH$_2$OH)— | 16 | 1 | H$_3$PO$_4$ |

TABLE 1-continued

| Compounds | R—N—R₁ | | —Z— | m/n | n | $HO-\underset{R_2}{\underset{|}{\overset{O}{\overset{\|}{P}}}}-R_3$ |
|---|---|---|---|---|---|---|
| 15 | CH₂CH₂OH | H | —HN(CH₂)₂O(CH₂)₂NH— | 15 | 1 | H₃PO₄ |
| 16 | (CH₂)₃OCH₃ | H | —HN—⟨C₆H₄⟩—CONH—⟨C₆H₄⟩—NH— | 16 | 0.7 | H₃PO₄ |
| 17 | CH₂CH₂OCH₃ | H | —N(C₂H₅)—CH₂—CH=CH—CH₂—N(C₂H₅)— | 17 | 1 | H₃PO₃ |
| 18 | H | H | —N(2,5-dimethylpiperazine)N— | 14 | 0.3 | $HO-\overset{\overset{O}{\|}}{\underset{HO}{P}}-O-\overset{\overset{O}{\|}}{\underset{OH}{P}}-O-\overset{\overset{O}{\|}}{\underset{OH}{P}}-OH$ |
| 19 | (CH₂)₄OCH₃ | H | —N(CH₂CH₂OH)—CH₂CH₂—NH— | 18 | 1 | H₃PO₄ |
| 20 | (CH₂)₂O(CH₂)₂OH | H | —HNCH₂CH₂NH— | 15 | 0.8 | H₃PO₃ |
| 21 | CH₂CH₂OH | CH₃ | —HN(CH₂)₂—NH—(CH₂)₂NH | 20 | 1 | H₃PO₄ |
| 22 | CH₂CH₂OCH₃ | H | —HN(CH₂)₃—N⟨piperazine⟩N—(CH₂)₃NH— | 19 | 1 | H₃PO₄ |
| 23 | (CH₂)₃OH | H | —HN(CH₂)₃—N(H)—(CH₂)₃NH— | 16 | 0.6 | H₃PO₄ |
| 24 | CH₂CH₂OH | H | —HN—C(CH₃)₂—⟨cyclohexyl⟩—C(CH₃)₂—NH— | 14 | 0.4 | $HO-\overset{\overset{O}{\|}}{\underset{HO}{P}}-\overset{CH_3}{\underset{NH_2}{C}}-\overset{\overset{O}{\|}}{\underset{OH}{P}}-OH$ |

The following examples illustrate the features of the present invention, without limiting them.

The salifying reaction between the intermediates with general formula (XIV) and the phosphorus-containing acids with general formula (XV) are confirmed by I.R. spectroscopic analysis carried out on the I.R. spectrophotometer Model Perkin Elmer 580 B with raster.

In fact, it was observed that an extremely good reference signal is constituted by the band relevant to the off-plane deformation of the triazinic ring: said band is at approximately 830–800 cm⁻¹ in the case of the not perturbed ring, and is at 795–760 cm⁻¹ in the case of the ring with salified amino groups.

EXAMPLE 1

184.5 g of cyanuric chloride and 700 cm³ of water are added to a reactor of 2 liters of capacity, equipped with stirrer, thermomemter, addition funnel, reflux condenser and cooling bath.

With cooling from the outside, 75 g of 2-methoxyethylamine and 40 g of sodium hydroxide dissolved in 150 cm³ of water are simultaneously added during a 3-hours time, with pH being kept at a value comprised within the range of from 5 to 7 and temperature being comprised within the range of from 0° to 3° C.

The reaction mixture is kept at the temperature of 0°–3° C. for a further 2 hours, then the resulting product is filtered off and is washed on the filter with water.

By drying the filter cake inside an oven at 50° C., under vacuum, 214.5 g of intermediate (XVI):

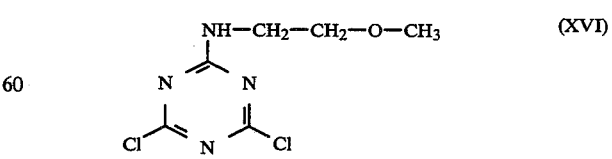

(XVI)

is obtained as a white crystal powder with melting point (m.p.)=73°–75° C., and with a chlorine content of 31.68% (theoretical value: 31.84%).

The structure of the intermediate was furthermore confirmed by N.M.R. analysis.

To the same reaction vessel of 2 liters of capacity, but equipped with heating bath, 800 cm³ of xylene, 50 cm³ of water and 100 g of intermediate (XVI) and then, with stirring, and during 20 minutes, 26.9 g of ethylenediamine, are added.

The temperature of the dispersion increases up to 60°–65° C.; it is adjusted at 75° C. by means of the external heating bath, and is stirred at that temperature for about 1 hour.

Then, 17.5 g of sodium hydroxide dissolved in 40 cm³ of water is added during a 2-hours time, and at the temperature of 75° C.

The temperature is increased up to 95° C. and the reaction mixture is kept stirred at that temperature for about 2 hours.

Then, 18.4 of sodium hydroxide dissolved in 40 cm³ of water is added during about 2 hours.

The temperature is gradually increased with water being removed by azeotropic distillation, until the boiling temperature of the solvent is reached.

The reaction mixture is kept refluxing for 10 hours, then the resulting mass is cooled down to room temperature, and the resulting product is filtered.

The filter cake is thoroughly pressed and is washed with plentiful water.

After oven drying at 100° C., 84.9 of intermediate (XVII):

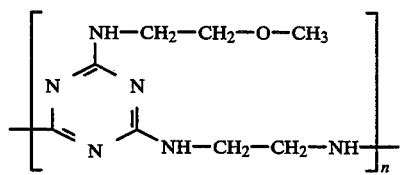

is obtained as a crystalline powder of white colour, with m.p. =182°–186° C. and with n=20.

500 cm³ of acetonitrile, 63.0 g of intermediate (XVII) and, with stirring, 36.3 g of phosphoric acid at 85% by weight are added to a 1-liter reactor equipped with stirrer, thermomemter, addition funnel, reflux condenser and heating bath.

The resulting reaction mixture is heated up to boiling, and is kept refluxing for 12 hours.

After cooling down to room temperature, the resulting product is filtered off and the filter cake is washed on the filter with acetonitrile.

After oven-drying the filter cake at 100° C., 89.1 g of the product:

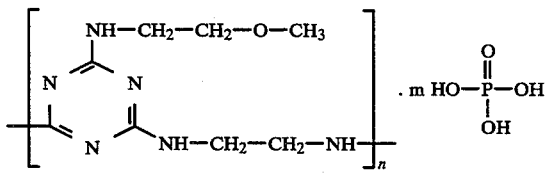

is obtained as a crystalline powder of white colour with m.p. =165°–170° C., with n=20 and m/n=1, and with a phosphorus content of 9.82% (theoretical value: 10.06%).

EXAMPLE 2

To the same reactor of Example 1, 800 cm³ of water and 184.5 g of cyanuric chloride are added.

By following the same procedure as disclosed in Example 1, 133 g of bis(2-methoxyethylamine) is added.

By continuing to operate according to the modalities shown in said Example, 260.8 g of intermediate (XVIII):

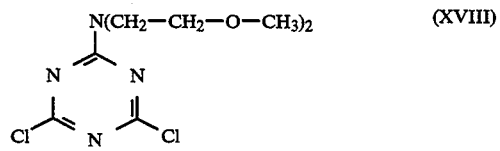

is obtained as a white crystal powder with m.p. =62°–65° C., and with a chlorine content of 25.08% (theoretical value: 25.27%).

The structure of the intermediate (XVIII) was furthermore confirmed by N.M.R. analysis.

To the same reaction vessel of 2 liters of capacity as of Example 1, 800 cm³ of xylene, 50 cm³ of water and 135 g of intermediate (XVIII) and then, with stirring, and during 15 minutes, 41.3 g of piperazine are added.

The temperature of the suspension increases up to 40°–45° C.

Then, still following the same operating modalities as disclosed in Example 1 (in this case, 38 g of sodium hydroxide is used), 136.4 of intermediate (XIX):

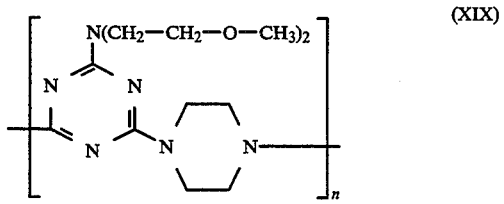

is obtained as a crystalline powder of white colour, with m.p. >300° C. and with n=18.

600 cm³ of acetonitrile, 88.2 g of intermediate (XIX) and, with stirring, 25.8 g of phosphorous acid are added to the same 1-liter reactor as of Example 1.

The resulting reaction mixture is heated up to its boiling temperature, and is kept refluxing for 12 hours.

After cooling down to room temperature, the resulting product is filtered off and the filter cake is washed on the filter with acetonitrile.

After oven-drying the filter cake at 100° C., 109.7 g of product:

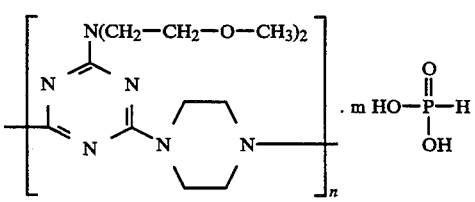

is obtained as a crystalline powder of white colour with m.p.=283°–287° C., with n=18 and m/n=1, and with a phosphorus content of 8.01% (theoretical value: 8.24%).

EXAMPLE 3

400 cm³ of acetone and 100 g of cyanuric chloride are added to the same 2-liter reactor as of Example 1.

The suspension is cooled down to 0°-5° C. and 23.4 g of piperazine is then added, during a 1-hour time.

Still at 0°-5° C., and during a 2-hour time, 23.3 g of piperazine and 10.8 g of sodium hydroxide dissolved in 50 cm³ of water are fed simultaneously, in such a way as to keep pH at a value of round 3.

The temperature is increased up to 20° C. during about 2 hours and 10.8 g of sodium hydroxide dissolved in 50 cm³ of water are simultaneously added, so as to keep pH at a value of round 5.

The temperature is further gradually increased from to 20°to 60° C., with a solution consisting of 21.8 g of sodium hydroxide in 100 cm³ of water being simultaneously fed.

The reaction mass is kept stirred at 60° C. for a further 2 hours, and then is cooled down to room temperature, and the resulting product is filtered off, and is washed on the filter, with water.

By drying the filter cake in an oven at 100° C., 104.9 g of intermediate (XX):

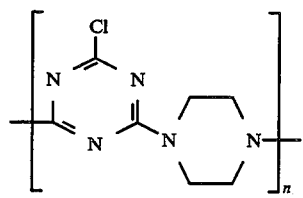
(XX)

is obtained as a crystalline powder of white colour, with m.p.>300° C. and with n=15, and with a chlorine content of 17.70% (theoretical value: 17.94%).

The structure of the intermediate was furthermore confirmed by I.R. spectroscopic analysis.

400 cm³ of water, 125 g of a solution of ammonium hydroxide at 30% by weight and 100 of intermediate (XX) are added to a steel reactor of 1 liter of capacity.

The reaction mixture is then heated to 150° C. and is kept at that temperature for 12 hours.

The reaction mixture is cooled down to room temperature, the resulting product is filtered off and the filter cake is washed on the filter, with water.

By oven-drying the filter cake in the oven at 100° C., 87.1 of intermediate (XXI):

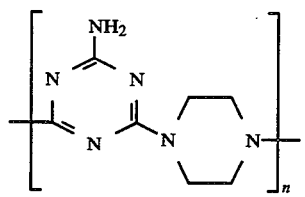
(XXI)

is obtained as a crystalline powder of white colour, with m.p.>300° C. and with n=15.

600 cm³ of acetonitrile, 53.4 g of intermediate (XXI) and, with stirring, 36.3 of phosphoric acid at 85% by weight are charged to a 1-liter reactor, equipped as in the preceding Examples.

The reaction mass is heated up to boiling temperature, and is kept refluxing for 14 hours.

Then, by proceeding analogously to as disclosed in Example 1, 82.1 g of product:

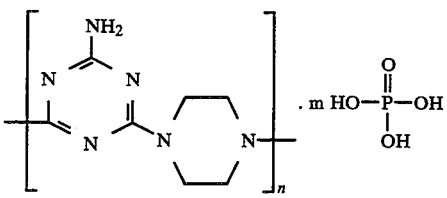

is obtained as a crystalline powder of white colour with m.p.>300° C., with n=15 and m/n=1, and with a phosphorus content of 11.06% (theoretical value: 11.23%).

EXAMPLE 4

To a 2-liter reactor equipped as in Example 1, 800 cm³ of xylene, 100 g of intermediate (XVI), 38.6 g of piperazine and 35.9 g of sodium hydroxide are added.

The reaction mass is heated up to its boiling temperature, and is kept refluxing for 24 hours.

At the end, the reaction mixture is cooled down to room temperature, the resulting product is filtered off and the filter cake is washed on the filter with plentiful water.

By drying the filter cake 100.8 g of intermediate (XXII):

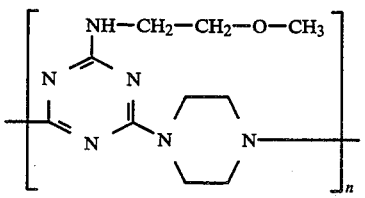
(XXII)

is obtained as a crystalline powder of white colour with m.p.>300° C., and with n=16.

500 cm³ of acetonitrile, 59 g of intermediate (XXII) and, with stirring, 30.2 of phosphoric acid at 85% by weight are charged to a 1-liter reactor, equipped as in the preceding Example 1.

The reaction mass is heated up to boiling temperature, and is kept refluxing for 14 hours.

Then, by proceeding analogously to as disclosed in Example 1, 82.4 g of product:

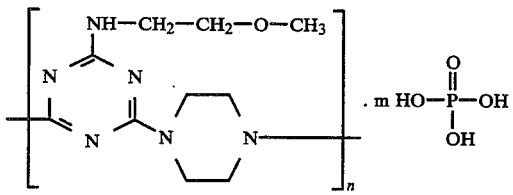

is obtained as a crystalline powder of white colour with m.p.>300° C., with n=16 and m/n=1, and with a phosphorus content of 9.41% (theoretical value: 9.28%).

EXAMPLE 5

To a 1-liter reactor equipped as in Example 1, 328 g of phosphorous acid and 82 g of acetonitrile are added. The reaction mixture is gradually heated up to 160° C. in 6 hours.

A crystalline product of white colour is formed.

The reaction mixture is subsequently cooled down to 80° C., 500 cm³ of water is then added to the reaction mixture with good stirring, then the reaction mixture is allowed to cool down to room temperature.

The resulting product is filtered off and the filter cake is washed on the filter with a little of water.

By drying the filter cake 290 g of 1-aminoethane-1,1-diphosphonic acid is obtained as a crystalline powder of white colour with m.p.=265°-270° C. (with decomposition), and with a phosphorus content of 29.4% (theoretical value: 30.24%).

600 cm³ of water and 71.2 g of intermediate (XXI) are charged to the same 1-liter reactor.

The reaction mass is heated up to 80° C. and 41.0 g of 1-aminoethane-1,1-diphosphonic acid is added with stirring.

The reaction mixture is heated up to boiling, and is kept approximately 8 hours under refluxing conditions.

The reaction mixture is then cooled down to room temperature, the resulting product is filtered off and the filter cake is washed on the filter, with water.

After drying the filter cake, 112.2 g of product:

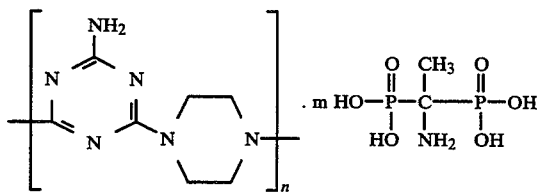

is obtained as a crystalline powder of white colour with m.p.>300° C., with n=15 and m/n=0.5, and with a phosphorus content of 10.87% (theoretical value: 11.05%).

EXAMPLE 6

To a 1-liter reactor equipped as in Example 1, 350 cm³ of xylene, 30 cm³ of water, 66.9 g of intermediate (XVI), and, with stirring and during about 15 minutes, 30.9 g of diethylenetriamine are added.

Then, by subsequently proceeding according to the same operating modalities as disclosed in Example 1 (in this case, 24 g of sodium hydroxide is used), 72.8 g of intermediate (XXIII):

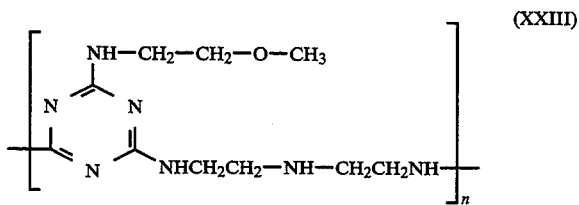

is obtained as a crystalline powder of white colour with m.p.>300° C., and with n=18.

600 cm³ of water, 75.9 g of intermediate (XXIII) and, with stirring and during 15 minutes, 61.8 g of a solution at 60% by weight of 1-hydroxyethane-1,1-diphosphonic acid are added to the same 1-liter reactor.

The reaction mass is heated up to boiling temperature, and is kept refluxing for 12 hours.

The reaction mass is cooled down to room temperature, the resulting product is filtered off and the filter cake is washed on the filter, with water.

By oven-drying the filter panel at 100° C., 111.8 g of product:

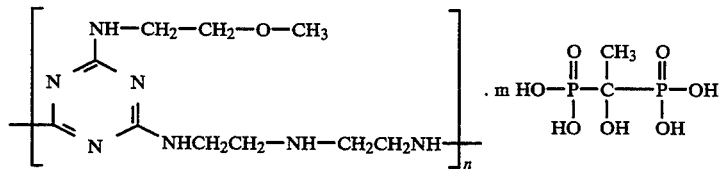

is obtained as a crystalline powder of white colour with m.p.>300° C., with n=18 and m/n=0.6, and with a phosphorus content of 9.64% (theoretical value: 9.88%).

EXAMPLES 7-15

By operating under analogous conditions to as disclosed in Examples 1-6, the products with general formula (I) are prepared, which are reported in following Table 2.

TABLE 2

| Example N. | R---N---R₁ | —Z— | m/n | n | $HO-\overset{O}{\underset{R_2}{\overset{\|}{P}}}-R_3$ | Melting point (°C.) | Phosphorus content, % Computed | Found |
|---|---|---|---|---|---|---|---|---|
| 7 | CH₂CH₂OH | H | —N⟨   ⟩N— | 20 | 1 | H₃PO₄ | >300 | 9.69 | 9.42 |
| 8 | CH₂CH₂CH₂OCH₃ | H | —N⟨   ⟩N— | 22 | 1 | H₃PO₄ | 218-224 | 8.91 | 8.78 |
| 9 | H | H | —N⟨   ⟩N— | 15 | 0.5 | H₃PO₄ | >300 | 6.83 | 6.67 |

TABLE 2-continued

| Example N. | R—N—R$_1$ | —Z— | m/n n | HO—P(=O)(R$_3$)(R$_2$) OH | Melting point (°C.) | Phosphorus content, % Computed | Found |
|---|---|---|---|---|---|---|---|
| 10 | H, H | —N(C$_4$H$_8$)N— (piperazine) | 15 1 | HO—P(=O)(OH)(C$_6$H$_5$) | >300 | 9.23 | 9.02 |
| 11 | CH$_2$CH$_2$OH, CH$_3$ | —HN(CH$_2$)$_6$NH— | 21 1 | H$_3$PO$_4$ | >300 | 8.52 | 8.68 |
| 12 | CH$_2$CH$_2$OCH$_3$, H | —HNC$_2$H$_4$—N—C$_2$H$_4$NH— | 18 1 | H$_3$PO$_3$ | >300 | 7.56 | 7.41 |
| 13 | CH$_2$CH$_2$OCH$_3$, H | —HN—C$_6$H$_4$—NH— | 16 1 | H$_3$PO$_4$ | >300 | 8.71 | 8.47 |
| 14 | H, H | —HNCH$_2$CH$_2$NH— | 17 0.4 | HO—P(=O)(OH)—O—P(=O)(OH)—OH | >300 | 11.11 | 10.96 |
| 15 | H, H | —N(C$_4$H$_8$)N— (piperazine) | 15 0.5 | HO—P(=O)(OH)—C(CH$_3$)(OH)—P(=O)(OH)—OH | >300 | 11.03 | 11.27 |
| 16 | tert.-C$_4$H$_9$, H | —N(C$_4$H$_8$)N— (piperazine) | 24 1 | H$_3$PO$_4$ | >300 | 9.33 | 9.48 |
| 17 | pyrrolidinyl | —N(C$_4$H$_8$)N— (piperazine) | 18 1 | H$_3$PO$_4$ | >300 | 9.39 | 9.21 |

TABLES 3 and 4

The tests reported in these tables relate to polymeric compositions containing the products of general formula (I) prepared according to the preceding examples.

Specimens consisting of approximately 3 mm thick slabs were prepared by moulding blends of granular polymers and additives, on a MOORE platen press, with a moulding time of 7 minutes under a pressure of 40 kg/cm$^2$.

On the resulting slabs, the self-extinguishment level was determined by measuring the oxygen index (L.O.I. according to ASTM D-2863/77) on a Stanton RedCroft instrument and applying the "Vertical Burning Test", which makes it possible the material to be classified at three levels (94 V-0, 94 V-1, 94 V-2, according to UL 94 standard procedures (issued by Underwriters Laboratories—U.S.A.).

In Table 3, the values are reported which were obtained by using an isotactic polypropylene in flake form having a Melt Flow Index of 12 and a content of insolubles in boiling n-heptane of 96% by weight.

In Table 4 the values are reported which were obtained by using low-density polyethylene pellets having a Melt Flow Index of 7; polystyrene pellets containing 5% by weight of butadiene rubber and having a Melt Flow Index of 9; thermoplastic polyurethane pellets of both polyester (ESTANE 54600[R] ex Goodrich) and polyether type (ESTANE 58300[R] ex Goodrich), with specific weights of 1.19 and 1.10 g/cm$^3$ respectively; an elastomeric ethylene-propylene copolymer with a % propylene content of 45; an acrylonitrile-butadiene-styrene terpolymer having a specific gravity of 1.06 g/cm$^3$, a Melt Flow Index of 1.6 and containing about 40% of acrylonitrile and styrene and 20% of butadiene.

TABLE 3

| Example N. | Product of Example N. | Parts by weight Product | PP[1] | AO[2] | APP[1] | L.O.I. (ASTM D 2863) | UL 94 3 mm |
|---|---|---|---|---|---|---|---|
| 18 | 1 | 11.0 | 77 | 1 | 11.0 | 32.2 | V0 |
| 19 | 2 | 12.0 | 75 | 1 | 12.0 | 32.0 | V0 |
| 20 | 3 | 5.4 | 80 | 1 | 13.6 | 35.0 | V0 |
| 21 | 3 | 19.5 | 70 | 1 | 9.5 | 33.3 | V0 |
| 22 | 4 | 4.0 | 83 | 1 | 12.0 | 30.0 | V2 |

TABLE 3-continued

| Example N. | Product of Example N. | Parts by weight | | | | L.O.I. (ASTM D 2863) | UL 94 3 mm |
|---|---|---|---|---|---|---|---|
| | | Product | PP[1] | AO[2] | APP[1] | | |
| 23 | 4 | 6.3 | 80 | 1 | 12.7 | 35.5 | V0 |
| 24 | 5 | 6.3 | 80 | 1 | 12.7 | 34.0 | V0 |
| 25 | 6 | 5.4 | 80 | 1 | 13.6 | 34.8 | V0 |
| 26 | 7 | 6.3 | 80 | 1 | 12.7 | 34.9 | V0 |
| 27 | 8 | 8.0 | 75 | 1 | 16.0 | 37.4 | V0 |
| 28 | 9 | 8.0 | 75 | 1 | 16.0 | 34.7 | V0 |
| 29 | 10 | 12.0 | 75 | 1 | 12.0 | 31.7 | V0 |
| 30 | 11 | 9.5 | 80 | 1 | 9.5 | 32.1 | V1 |
| 31 | 12 | 6.3 | 80 | 1 | 12.7 | 33.0 | V0 |
| 32 | 13 | 7.0 | 78 | 1 | 14.0 | 30.8 | V1 |
| 33 | 14 | 6.3 | 80 | 1 | 12.7 | 32.4 | V0 |
| 34 | 15 | 4.6 | 83 | 1 | 11.4 | 29.8 | V2 |
| 35 | 15 | 6.3 | 80 | 1 | 12.7 | 34.8 | V0 |
| 36 | 16 | 12.0 | 75 | 1 | 12.0 | 34.4 | V0 |
| 37 | 17 | 12.0 | 75 | 1 | 12.0 | 36.0 | V0 |
| 38 | 15 | 8.0 | 75 | 1 | *16.0 | 37.9 | V0 |
| 39 | 4 | 12.0 | 75 | 1 | [3]12.0 | 35.8 | V0 |

[1]PP = polypropylene
APP = ammonium polyphosphate - Exolit 422 (®) (Hoechst)
* = APP microencapsulated with Exolit 462 (®) melamine-formaldehyde resin (Hoechst)
[2]AO = Antioxidant
A mixture constituted by 2 parts of dilauryl-thiopropionate and 1 part of pentaerythritol tetra-[3-(3,5-di-tert.-butyl-4-hydroxyphenyl)-propionate]
[3] = APP was replaced by monoammonium salt of 1-aminoethane-1,1-diphosphonic acid.

TABLE 4

| Example N. | Polymeric support | Product of Example N. | Parts by weight | | | | L.O.I. (ASTM D 2863) | UL 94 3 mm |
|---|---|---|---|---|---|---|---|---|
| | | | Product | Polymer | AO[2] | APP[1] | | |
| 40 | LDPE | 1 | 7.3 | 70 | 1 | 21.7 | 33.7 | V0 |
| 41 | | 3 | 6.4 | 70 | 1 | 22.5 | 32.0 | V0 |
| 42 | | 4 | 5.3 | 75 | 1 | 18.7 | 32.1 | V0 |
| 43 | | 15 | 14.5 | 70 | 1 | 14.5 | 33.2 | V0 |
| 44 | HIPS | 3 | 8.5 | 65 | 1 | 25.5 | 32.7 | V0 |
| 45 | | 10 | 7.3 | 70 | 1 | 21.7 | 31.4 | V0 |
| 46 | PU (ester) | 3 | 16.0 | 75 | 1 | 8.0 | 34.2 | V0 |
| 47 | | 5 | 16.0 | 75 | 1 | 8.0 | 33.4 | V0 |
| 48 | PU (ether) | 5 | 19.4 | 70 | 1 | 9.7 | 31.4 | V0 |
| 49 | PP/PE | 4 | 12.0 | 75 | 1 | 12.0 | 34.0 | V0 |
| 50 | ABS | 10 | 7.0 | 71 | 1 | 21.0 | 30.8 | V0 |

[1]APP = ammonium polyphosphate - Exolit 422 (®) (Hoechst)
[2]LDPE = Low-density polyethylene
HIPS = polystyrene containing 5% of butadiene rubber
(ester) PU = Polyester polyurethane
(ether) PU = Polyether polyurethane
PP/PE = propylene-ethylene copolymer
ABS = acrylonitrile-butadiene-styrene terpolymer
[3]AO = Antioxidant
A mixture constituted by 2 parts of dilauryl-thiopropionate and 1 part of pentaerythritol tetra-[3-(3,5-di-tert.-butyl-4-hydroxyphenyl)-propionate]

We claim:

1. Salts of triazinic compounds with phosphorus oxy-acids, having the general formula (I):

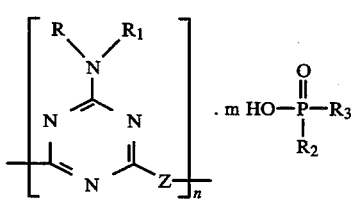

wherein:
R is H or

—[—$C_pH_{2p}$—]—O—$R_4$ in which p is an integer comprised within the range of from 2 to 8; and $R_4$ is H; ($C_1$–$C_8$)-alkyl; ($C_2$–$C_8$)-alkenyl; —[—$C_qH_{2q}$—]—O—$R_5$, in which q is an integer comprised within the range of from 1 to 4; and $R_5$ is H or ($C_1$–$C_4$)-alkyl; ($C_6$–$C_{12}$)-cycloalkyl or alkylcycloalkyl; $R_1$ is ($C_1$–$C_4$)-alkyl or R; or the moiety:

is replaced by a heterocyclic radical bonded to the triazinic ring through the nitrogen atom; wherein said heterocyclic radical is selected from the group consisting of aziridine, pyrrolidine, piperidine, and piperazine radicals;

n is an integer comprised within the range of from 2 to 50;

m is a numeral smaller than, or equal to, n;

z is a divalent or polyvalent radical falling within the scope of one of following formulae:

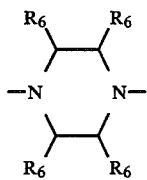 (II)

wherein the —$R_6$ radicals, which may be the same, or different from each other, are hydrogen or ($C_1$–$C_4$)-alkyl;

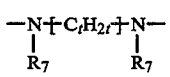 (III)

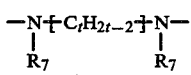 (IV)

wherein t is an integer comprised within the range of from 2 to 14; $R_7$ is hydrogen, ($C_1$–$C_4$)-alkyl, ($C_2$–$C_6$)-alkenyl, ($C_1$–$C_4$)-hydroxyalkyl;

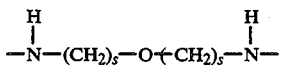 (V)

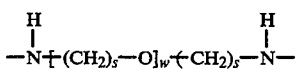 (VI)

wherein s is an integer comprised within the range of from 2 to 5 and w is an integer comprised within the range of from 1 to 3;

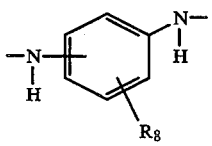 (VII)

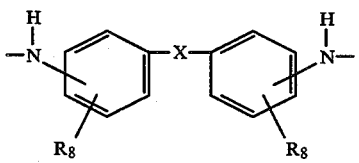 (VIII)

wherein:

X is a direct —C—C—; O; S; S—S; SO; $SO_2$; NH; $NHSO_2$; NHCO; N=N; $CH_2$ bond;

$R_8$ is hydrogen; hydroxy; ($C_1$–$C_4$)-alkyl; ($C_1$–$C_4$)-alkoxy;

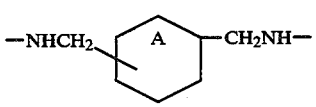 (IX)

wherein "A" can be a saturated or unsaturated cycle;

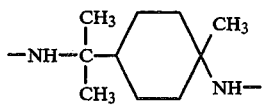 (X)

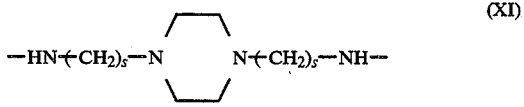 (XI)

wherein s has the above defined meaning;

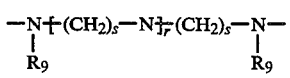 (XII)

wherein;

$R_9$ is hydrogen or ($C_1$–$C_4$)-alkyl;

r is an integer comprised within the range of from 1 to 5;

the indexes s, which are the same, or may be different from each other, have the above defined meaning;

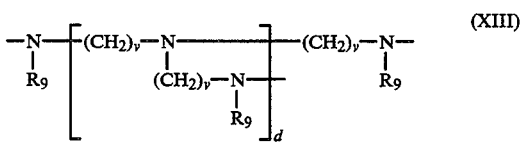 (XIII)

wherein:

$R_9$ has the above defined meaning;

v is an integer comprised within the range of from 2 to 4;

d is either 1 or 2;

$R_2$ is H; OH; —O—($C_1$–$C_8$)-alkyl; —O—($C_6$–$C_{12}$)-aryl, possibly substituted with a ($C_1$–$C_8$)-alkyl; ($C_7$–$C_{16}$)-aralkyl; ($C_1$–$C_4$)-alkyl possibly substituted with a carboxy group; ($C_6$–$C_{12}$)-aryl;

$R_3$ is H; OH; —O—($C_1$–$C_8$)-alkyl; —O—($C_6$–$C_{12}$)-aryl, ($C_1$–$C_4$)-alkyl; ($C_6$–$C_{12}$)-aryl;

$R_3$ furthermore is:

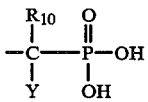

wherein:

$R_{10}$ is hydrogen or ($C_1$–$C_{12}$)-alkyl;

Y is OH or $R_{10}$;

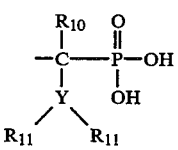

wherein:

$R_{10}$ has the same meaning as defined hereinabove and $R_{11}$ radicals, which are the same, or may be different from each other, are hydrogen or ($C_1$–$C_4$)-alkyl;

or the moiety:

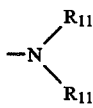

is replaced by a heterocyclic radical bonded to the carbon atom through the nitrogen atom wherein said heterocyclic radical is selected from the group consisting of azirdine, pyrrolidine, piperidine, or piperazine radicals;

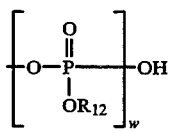

wherein:
$R_{12}$ is hydrogen or $(C_1-C_8)$-alkyl; and
w has the same meaning as defined hereinabove;

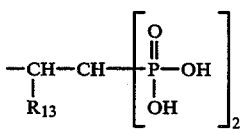

wherein:
$R_{13}$ is hydrogen or hydroxy;

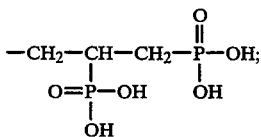

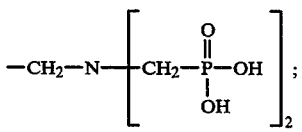

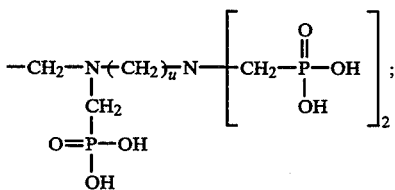

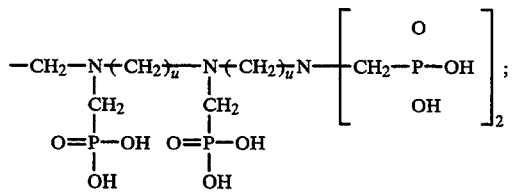

wherein:
u has the same meaning as defined above;
or
$R_2$ and $R_3$, taken together, may constitute a cyclic structure having the formula:

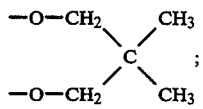

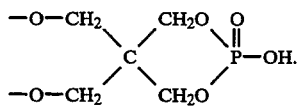

2. Salts of triazinic compounds with phosphorus oxyacids according to claim 1, in which said phosphorus acid is selected from: hypophosphorous acid; phosphorous acid; phosphoric acid; pyrophosphoric acid; tripolyphosphoric acid; ethane-1,1,2-triphosphonic acid; 2-hydroxyethane-1,1,2-triphosphonic acid; propane-1,2,3-triphosphonic acid; isopropylphosphoric acid; n-butylphosphoric acid; di-n-butylphosphoric acid; di-isopropylphosphoric acid; di-n-pentylphosphoric acid; isooctylphosphoric acid; hexylphosphoric acid; 2-ethylhexylphosphoric acid; methylphosphonic acid; ethylphosphonic acid; n-propylphosphonic acid; n-butylphosphonic acid; aminomethylphosphonic acid; phenylphosphoric acid; phenylphosphonic acid; phenylphosphinic acid; di-n-butylpyrophosphoric acid; di-(2-ethylhexyl)pyrophosphoric acid; octylphenylphosphoric acid; 2-methylbenzylphosphonic acid; 1-aminoethane-1,1-diphosphonic acid; 1-hydroxyethane-1,1-diphosphonic acid; 1-hydroxydodecane-1,1-diphosphonic acid; 1-(N-methylamino)-ethane-1,1-diphosphonic acid; N,N-dimethylaminoethane-1,1-diphosphonic acid; N-butyl-aminomethane-1,1-diphosphonic acid; phosphonoacetic acid; 2-phosphonopropionic acid; 3-phosphonopropionic acid; 2-phosphonobutyric acid; 4-phosphonobutyric acid; 2-hydroxy-5,5-dimethyl-2-oxo-1,3,2-dioxophosphorinane; 3,9-dihydroxy-2,4,8,10-tetraoxo-3,9-diphosphaspiro-[5,5]-undecane-3,9-dioxido; amino-tris(methylenephosphonic) acid; ethylenediaminotetra(methylene-phosphonic) acid; hexamethylenediaminotetra(methylene-phosphonic) acid; diethylenetriaminopenta(methylenephosphonic) acid; and so forth.

* * * * *